United States Patent [19]
Cuny et al.

[11] Patent Number: 5,626,608
[45] Date of Patent: May 6, 1997

[54] SURGICAL INSTRUMENT HAVING LOCKING HANDLE

[75] Inventors: Douglas J. Cuny, Bethel; Ernie Aranyi, Easton; Paul A. Matula, Brookfield, all of Conn.

[73] Assignee: United States Surgical Corporation, Norwalk, Conn.

[21] Appl. No.: 625,454

[22] Filed: Mar. 29, 1996

[51] Int. Cl.⁶ .............................. A61B 17/00; A61B 1/00
[52] U.S. Cl. ........................... 606/205; 600/131; 128/751
[58] Field of Search .................. 606/205–211, 26, 606/51–52; 128/4, 7, 751; 604/61

[56] References Cited

U.S. PATENT DOCUMENTS

| | | |
|---|---|---|
| Re. 32,214 | 7/1986 | Schramm . |
| 1,310,982 | 7/1919 | Davis . |
| 1,606,497 | 11/1926 | Berger . |
| 2,790,437 | 10/1957 | Moore . |
| 4,611,595 | 9/1986 | Klieman et al. . |
| 4,616,650 | 10/1986 | Green et al. . |
| 4,643,190 | 2/1987 | Heimberger . |
| 4,662,371 | 5/1987 | Whipple et al. . |
| 4,712,545 | 12/1987 | Honkanen . |
| 5,009,661 | 4/1991 | Michelson . |
| 5,031,814 | 7/1991 | Tompkins et al. . |
| 5,085,661 | 2/1992 | Moss . |
| 5,147,357 | 9/1992 | Rose et al. . |
| 5,174,300 | 12/1992 | Bales et al. . |
| 5,176,702 | 1/1993 | Bales et al. . |
| 5,258,004 | 11/1993 | Bales et al. . |
| 5,478,351 | 12/1995 | Meade et al. . |
| 5,483,952 | 1/1996 | Aranyi . |
| 5,499,992 | 3/1996 | Meade et al. . |

FOREIGN PATENT DOCUMENTS

| | | |
|---|---|---|
| 065054 | 11/1982 | European Pat. Off. . |
| 8311392 | 4/1983 | Germany . |
| 1544414 | 2/1990 | U.S.S.R. . |
| 2044108 | 10/1980 | United Kingdom . |

*Primary Examiner*—Michael Powell Buiz
*Assistant Examiner*—Nancy Connoly Mulcare

[57] ABSTRACT

An endoscopic or laparoscopic surgical instrument is disclosed having a handle assembly including a barrel portion, stationary handle and a pivoting handle. A body assembly includes a pair of coaxial members attached at one end to the handle assembly, and an inner rod member slidable within an outer tube member in response to movement of the pivoting handle of the handle assembly. The body assembly terminates at an end remote from the handle assembly in a reciprocatingly movable tool mechanism. A first toothed ratchet mechanism is associated with the pivoting handle, and a second toothed mating ratchet mechanism is operatively associated with the first toothed ratchet mechanism for selectively locking the first toothed ratchet mechanism and the pivoting handle in one of a plurality of selectable positions to thereby position the inner rod member and the movable tool mechanism in predetermined selectable positions. A finger operable trigger member is operatively associated with the second toothed ratchet mechanism for selectively engaging and disengaging the first and second ratchet mechanisms to thereby selectively lock and unlock the movable tool mechanism.

14 Claims, 4 Drawing Sheets

SURGICAL INSTRUMENT HAVING LOCKING HANDLE

BACKGROUND OF THE INVENTION

1. Field of the Invention

A surgical instrument is disclosed, and more particularly relates to a handle for an endoscopic or laparoscopic surgical instrument having reciprocating jaw members which pivot toward and away from each other in response to opening and closing movements of the handle members, where movement of the handle members is translated through an elongated tubular body member to open and close the jaw mechanism. The present invention further relates to a ratchet mechanism which is internally disposed within the handle to provide incremental positioning and selective release of the jaw members in relation to each other.

2. Discussion of the Prior Art

In the prior art, various endoscopic surgical instruments are disclosed which utilize elaborate and complex mechanisms for opening and closing handle members and jaw members to facilitate use of the device at a surgical site. Certain devices are of intricate construction in which a linkage mechanism for opening and closing the jaws requires numerous moving parts, while a sliding arrangement is provided between two extended rod members to activate the linkage mechanism in response to movement of the handle members. Furthermore, it is often necessary for the surgeon, or an assistant, to maintain a constant force on the handles to keep the jaw mechanism closed in the event that the instrument is a grasping or gripping device such as forceps, needle holders, or retractors. This limits the surgeon's range, and in the case of an assistant, often requires additional personnel to be present in the operating room, thus restricting movement in an already confined area.

To alleviate this problem, it has been known to provide locking mechanisms on the handles of the surgical instruments which allow the surgeon to lock or clamp the jaw members in place to free the surgeon's hands to operate additional instruments during the course of the operation. Furthermore, such mechanisms free the surgical assistant to support the surgeon and eliminate the need for additional assistants. Some typical locking devices include arm members which extend between the handles so that a series of ridges or ribs on each arm member engage corresponding ridges on the opposite arm to lock the handles in position. Bending one arm in relation to the other releases the locking mechanism.

One disadvantage associated with these known devices concerns the release of the locking mechanism for subsequent movement of the jaw members to remove or reposition the instrument. Generally, the arm members of locking mechanisms are constructed of a resilient material, such as stainless steel or rigid plastic, and the locking forces which hold the arm members in engagement are generated by the natural flexing and biasing of the material of which the arm members are constructed. To release the locking mechanism, the arms must be disengaged by overcoming the locking forces of the arms. Typically, this is accomplished by manually flexing the arms away from each other, necessitating the use of two hands, one to grasp the instrument, and the other to forcibly move the arm members. This, of course, requires the surgeon (or assistant) to release the mechanism, thereby providing a distraction from the surgeon's primary function. This factor also reduces the effectiveness of the surgeon during the operation, particularly in an emergency.

Another disadvantage of these known devices is that often such typical locking mechanisms cannot be overridden; that is, the mechanism is always engaged, thereby preventing free movement of the handle and jaw mechanism. This usually causes the surgeon to choose an instrument of one type or another, i.e., one having a locking mechanism or one having no locking mechanism. As a result, the surgeon may demand that all types of such instruments are present during an operative procedure thereby lending to an overabundance of instruments in the operating room and further complicating the procedure.

Lastly, locking mechanisms located on the handles may require particular procedures for sterilization, packaging and storage, as well as in normal handling in the operating room. Unwanted accumulation of debris may clog the ribs of the locking mechanism thus reducing its effectiveness. Additionally, this design may not be suitable for an instrument designed for multiple uses and such clogging may cause damage to the ribs during packaging or storage and may destroy the ribs, rendering the locking mechanism useless.

U.S. Pat. No. 1,452,373 to Gomez discloses a typical locking mechanism for a surgical instrument, in which a plurality of ribs are provided on an extension of the handle member which engage a similar rib member on the opposite handle. Once engaged, the handles must be moved away from each other perpendicular to their longitudinal to disengage the locking mechanism to release the jaw mechanism.

U.S. Pat. No. 4,896,661 to Bogerr et al. disclose a surgical instrument having a ratchet mechanism positioned on the handle members which includes a curved rack member attached to one handle member which passes through a slot in the other handle member. A releasable pawl member is provided on the second handle to engage the rack member and provide a means for releasing the ratchet.

U.S. Pat. No. 4,935,027 to Yoon discloses a surgical instrument having a ratchet mechanism positioned between the handle members. A rack member is provided which extends from one handle and passes through a slot in the second handle to lock the handles in place. Pivoting the rack member away from corresponding grooves in the slot will release the ratchet mechanism.

U.S. Pat. No. 4,428,374 to Auburn discloses a surgical instrument having means for positioning and holding the handle members in relation to each other. A rack member is provided on one handle member which extends through a slot in the second handle member in which a releasable pawl mechanism is provided to engage and disengage the ratcheting mechanism.

The novel surgical instrument disclosed herein overcomes the disadvantages encountered in the prior art and provides a precise instrument which is easy to manufacture and efficient to use, and which eliminates many of the moving parts required by prior art devices. Also, the present instrument incorporates many features which are of use to the surgeon during an operation, including an internal ratcheting mechanism to provide for incremental movement of the tool mechanism and locking of the jaws if desired, while maintaining a lightweight construction in an easy to handle device in which all of the features may be operated with one hand. Furthermore, the features are so positioned so as to provide a maximum line of sight for the surgeon without obstructing the view to the surgical site.

SUMMARY OF THE INVENTION

The present invention provides a novel endoscopic or laparoscopic surgical device which incorporates many features necessary for endoscopic or laparoscopic surgical procedures, and provides a lightweight and easy to use device which may be operated with one hand. The device includes an internal ratcheting mechanism which provides for incremental positioning of a tool mechanism at the distal end for performing the surgical procedure. The device is relatively simple to manufacture, and may incorporate any one of a series of jaw mechanisms or other surgical working tools for various types of surgical procedures. The device is a high precision instrument which eliminates the need for numerous moving parts as generally associated with such devices. This feature reduces instances of mechanical failure which otherwise require expensive repair or ultimate destruction of the instrument.

The endoscopic or laparoscopic surgical instrument of the present disclosure comprises a handle assembly, an elongated body assembly, and a ratchet mechanism positioned within the handle assembly. The handle assembly includes a stationary handle and pivoting handle, attached to the barrel portion on one side, and the body assembly is attached to the barrel portion on the other side, and extends therefrom. The body assembly consists of an outer tubular member and an inner rod member which coaxially passes within the outer tubular member. The rod member is attached to the pivoting handle, while the tubular member is secured in a conventional manner to the barrel portion which extends into the stationary handle. As the pivoting handle moves, the rod member slidably reciprocates within the outer tube member.

Attached to a distal end of the body assembly is the tool mechanism which opens and closes in response to movement of the pivoting handle in relation to the stationary handle. The tool mechanism may comprise a pair of jaw members wherein one or both jaw members open and close to perform various endoscopic or laparoscopic surgical procedures. The jaw mechanism includes, but is not limited to, a scissor device, a dissecting device, a grasping device, a retractor device, and like mechanisms.

The present apparatus also includes a rotatable knob on the outer tubular member to allow the elongated body assembly and jaw mechanism to rotate to position the jaws at desired angles to the longitudinal axis during the surgical procedure. Preferably, the rotatable knob is secured to the outer tube and positioned in a slot which passes through the barrel portion of the stationary handle, so that a surgeon may rotate the knob, and consequently the body assembly and jaw mechanisms, through the use of the thumb while holding the stationary handle with the fingers. This frees the surgeon's other hand to simultaneously operate another instrument during surgery.

A novel feature of the present instrument is the provision of a ratchet mechanism located inside the handle and a pivoting handle of the handle assembly to provide for incremental movement of the jaw mechanism. Since it is located inside the handle assembly, it is not subjected to environmental conditions which can result in clogging or damage to the ratchet mechanism during handling and storage. Furthermore, the novel ratchet mechanism of the present instrument provides for simple handling and maneuvering during the surgical procedure and allows the surgeon to operate the device with one hand, thus freeing the other hand for performing other functions during the surgical procedure.

The ratchet mechanism of the present invention includes a trigger mechanism for engaging and disengaging the ratchet feature. In a preferred embodiment, a trigger is pivotably attached to the stationary handle and has a lower portion forming trigger teeth for engagement with ratchet teeth formed on the pivoting handle. The trigger is biased by a leaf spring which maintains the trigger teeth in engagement with the ratchet teeth of the pivoting handle. When depressed, the trigger overcomes the force of the leaf spring and pivots the trigger teeth away from the ratchet teeth to release the ratchet mechanism. If the trigger is continually pressed, the ratchet mechanism is overridden and the device functions as a conventional surgical instrument.

Another novel feature of the present invention is the provision of a spring member disposed within the barrel portion to bias the pivoting handle proximally. The spring member, preferably a coil spring, is attached at one end to the barrel portion and at the other to the pivoting handle, biases the ratchet teeth proximally providing firm engagement with the trigger teeth.

In the preferred embodiment, all the above features are incorporated into a single endoscopic and laparoscopic surgical instrument, so that the instrument has rotational and ratcheting capabilities. However, the instrument of the present invention is constructed with at least the ratcheting capabilities to provide for incremental adjustment of the tool mechanism during a surgical procedure.

The present instrument provides features which may be used by a surgeon using one hand. While the ratchet mechanism is located inside the handle assembly, it may also be overridden from outside the instrument to allow for full movement of the handles of the device. Furthermore, as noted, the ratchet mechanism may be operated at any orientation of the tool mechanism.

BRIEF DESCRIPTION OF THE DRAWINGS

Preferred embodiments of the present surgical apparatus are disclosed hereinbelow with reference to the drawings wherein.

DESCRIPTION OF THE PREFERRED EMBODIMENTS

Figure 1:
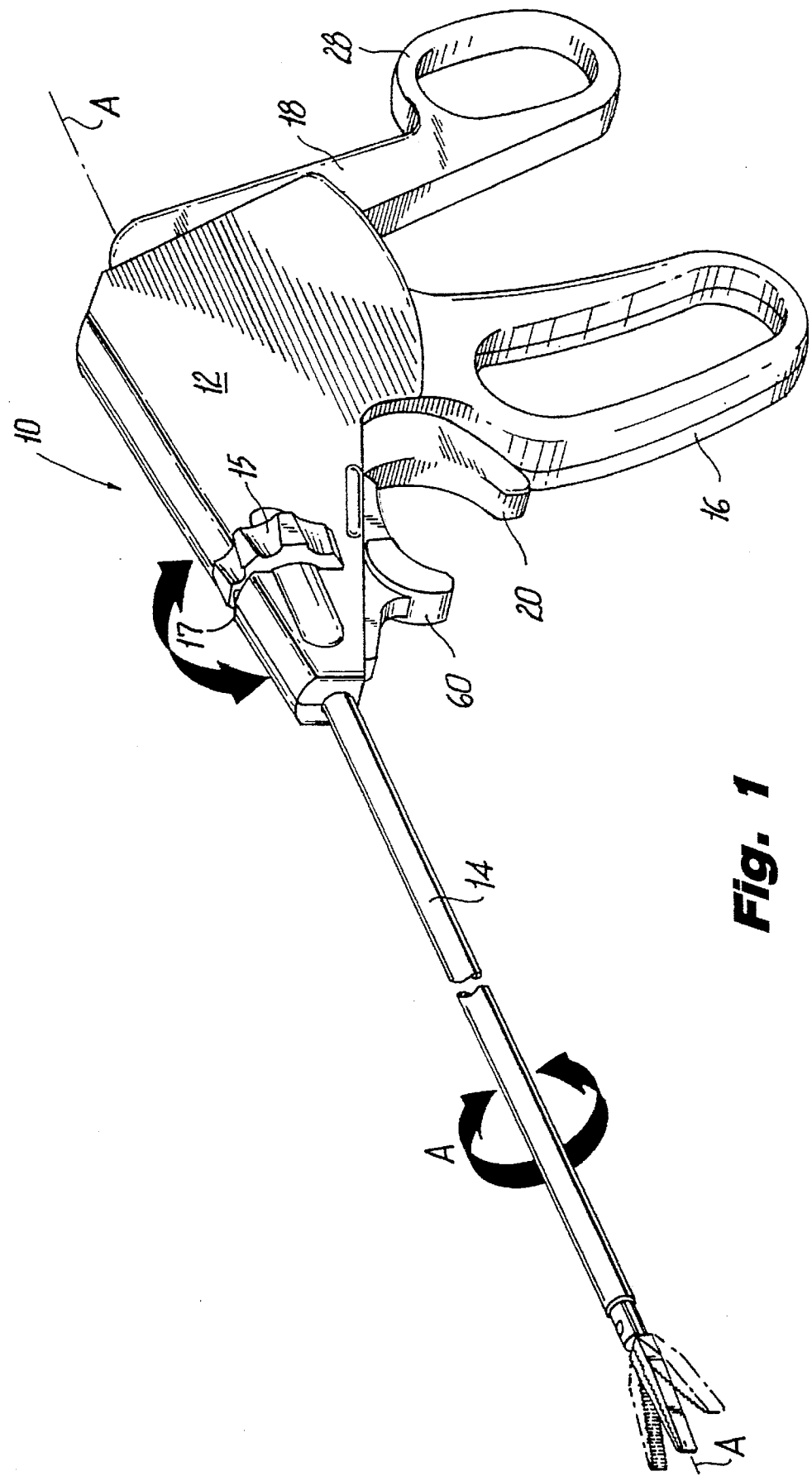
FIG. 1 is a perspective view of an endoscopic surgical instrument in the form of an endoscopic grasping device according to a preferred embodiment.

Referring to FIG. 1, there is shown a perspective view of an endoscopic grasping apparatus 10 having handle section 12 and elongated tubular endoscopic section 14 extending distally from the distal end of the handle section. Handle section 12 includes fixed handle 16 and pivotal control handle 18, the structure and function of which will be described in further detail. Furthermore, finger operable trigger 20 is provided to lock and unlock the pivotal handle in selected positions as will be described. Rotatable knob 15 is positioned within slot 17 of handle 12 and can be rotated in either direction to rotate the endoscopic section 14 in the directions shown by arrow "A" about longitudinal axis A—A.

Figure 2:
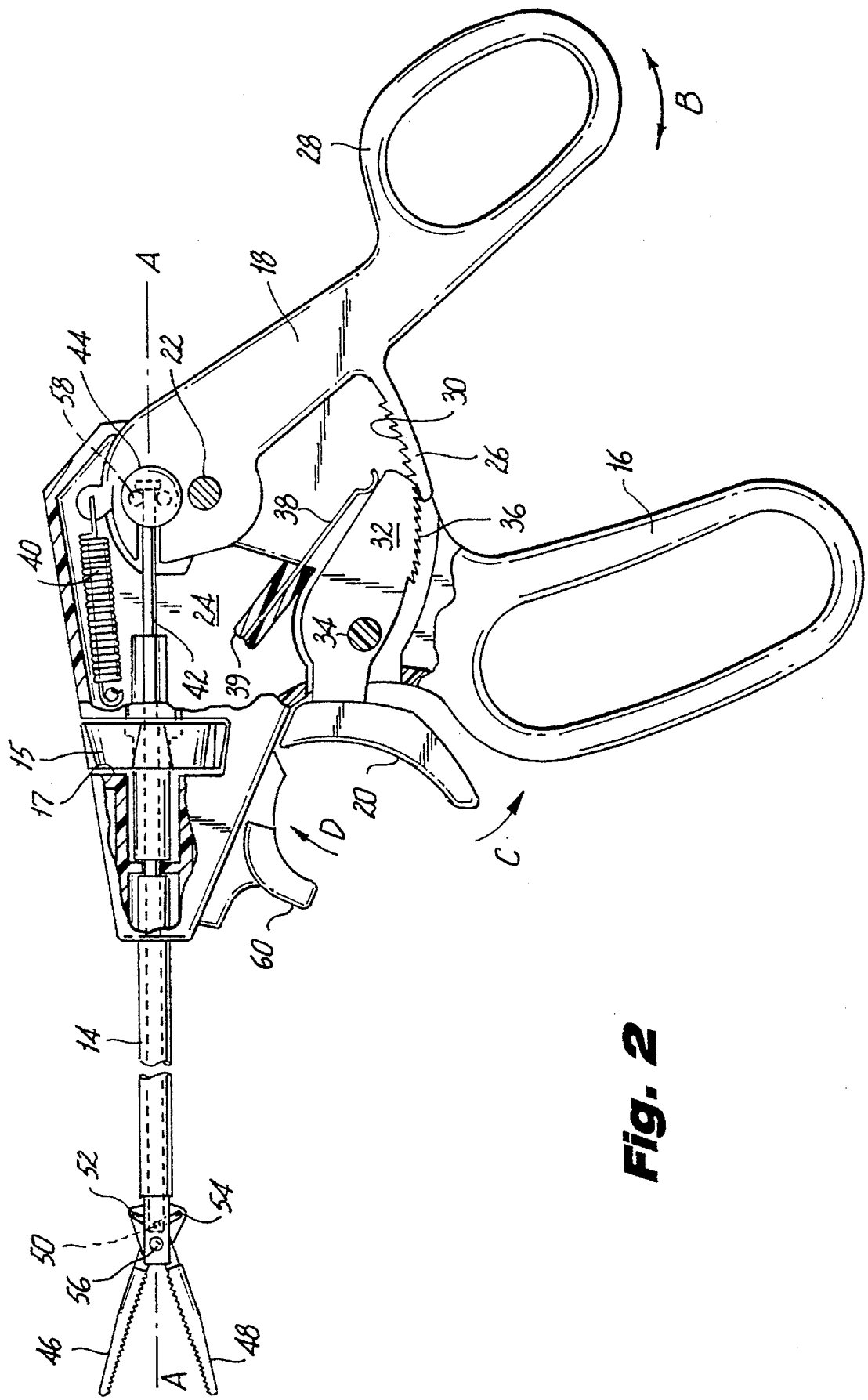
FIG. 2 is a side elevational view of the device of FIG. 1, partially in cross-section, and illustrating the ratchet-type locking mechanism with the grasper jaws locked in the open position.

Referring now to FIG. 2, a side elevational view, partially in cross-section, of the apparatus of FIG. 1, is illustrated. Handle 18 is pivotally mounted by pivot pin 22 to frame 24 for pivotal movement in the fore and aft directions illustrated by arrow "B". Handle 18 includes an arcuate section 26 extending in a distal direction from a location midway between pivot pin 22 and thumb ring 28, and includes a line of successive connected upstanding teeth 30. Finger operable trigger 20 in turn includes a proximally extending mating lock member 32 having downwardly extending teeth 36 which are dimensioned and shaped to mate with the upwardly extending teeth 30 of arcuate section 26. Member 32 is pivotably mounted to frame 24 by pivot pin 34 such that downward movement of trigger 20 in the direction of arrow "C" causes member 32 to pivot upwardly about pivot pin 34, and upward movement of trigger 20 in the direction of arrow "D" causes member 32 to pivot downwardly. When trigger 20 is moved proximally by the surgeon's forefinger and made to pivot in the direction of arrow "C", member 32 moves upwardly away from arcuate section 26 thereby creating a non-ratcheting handle by disengaging teeth 36 from teeth 30. However, if the surgeon does not maintain finger pressure on trigger 20, member 32 will engage arcuate section 26 and create a ratcheting handle.

Leaf spring 38 is fixed to the frame 24 at one end by attachment to fixture 39 and permitted to resiliently flex at the free end toward and away from member 32. When trigger 20 is released by the surgeon, arcuate section 32 pivots downwardly under the downward bias force of leaf spring 38 thus causing teeth 36 of member 32 to engage teeth 30 of arcuate section 26 and locking the members in position. Distal and proximal pivotal movement of handle 18 in the directions of arrow "B" is accomplished by the surgeon inserting the thumb in thumb ring 28. When the trigger 20 is moved proximally to release the locking teeth 36 from teeth 30 the surgeon is free to pivot handle 18 proximally and distally in the directions of arrow "B". The force of coil spring 40 serves to bias the pivotal handle in the proximal direction, while the force provided by the surgeon's thumb in the distal direction resists the coil spring force causing it to extend in length. When pivotal handle 18 is in the upward position under the influence of coil spring 40, the grasping jaws 46, 48 are in the open position.

Figure 3:
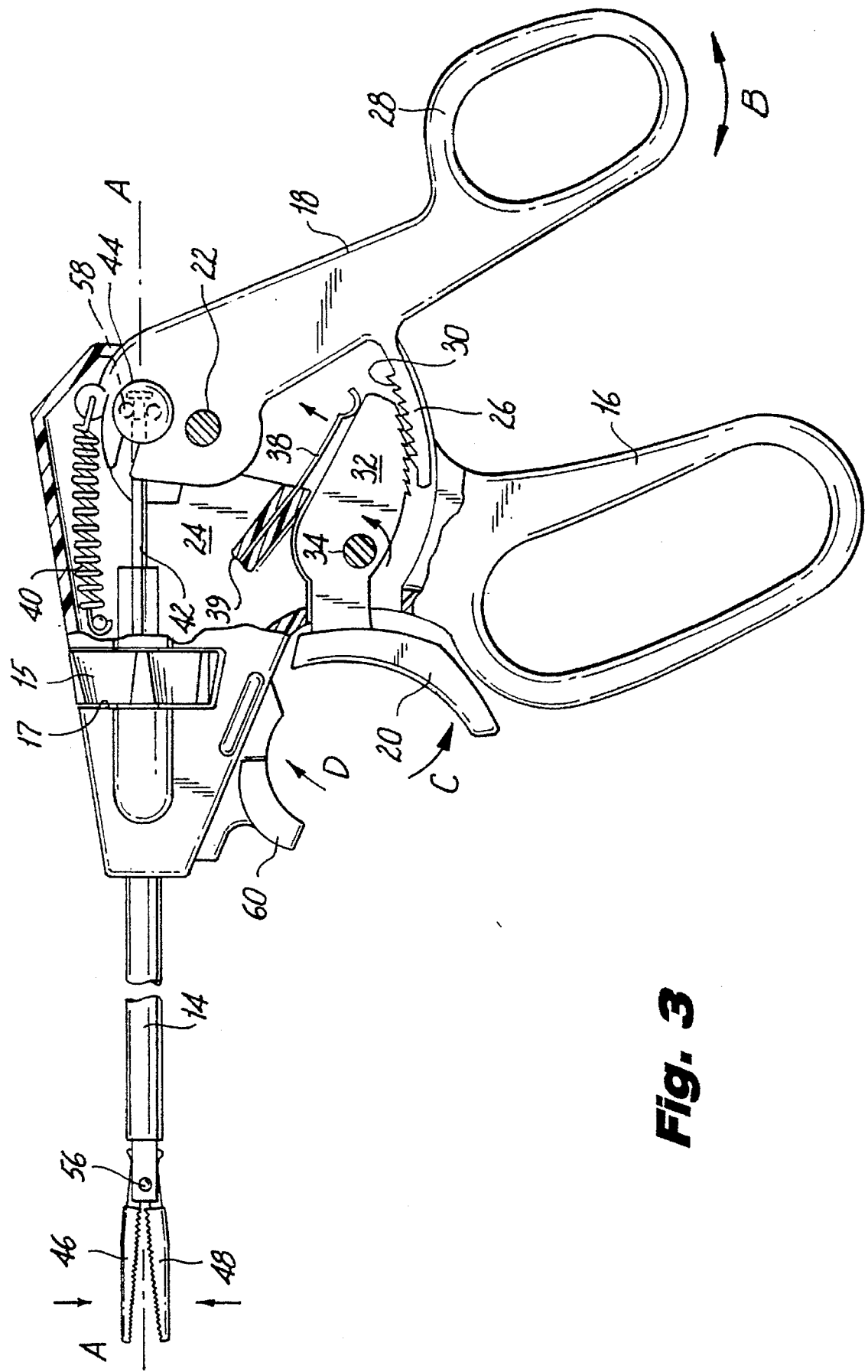
FIG. 3 is a view similar to FIG. 2 with the jaws in a partially closed condition and the ratchet mechanism in a partially engaged position.

In operation, the surgeon grasps the handle by inserting three fingers into fixed finger ring 16 with the thumb inserted into thumb ring 28, leaving the forefinger free to operate the trigger 20. By depressing trigger 20 in the proximal direction the lock member 32 pivots upwardly thus releasing teeth 36 from teeth 30 thereby permitting free proximal and distal pivotal movement of pivotal handle 18. Pivotal movement of handle 18 causes corresponding respective distal and proximal movement of elongated rod 42 which is connected to the upper portion of handle 18 and rotatably supported by the bearings of joint 44 shown schematically in the FIGS. 2 and 3.

Referring again to FIGS. 2–4, joint 44 permits proximal and distal movement of rod 42 while permitting it to rotate about a longitudinal axis A—A extending centrally thereafter along the endoscopic section 14. The proximal and distal movement of rod 42 in turn causes opening and closing pivotal movement of jaws 46 and 48 in a known manner, i.e. by transverse pin 50 connected to rod 42 translating proximally and distally within angled slots 52,54 provided in the rear portion of each respective jaw at locations proximal of the common pivot pin 56 of the jaws. Thus downward and distal movement of pivotal handle 18 in the downward direction illustrated by arrow "B" in FIG. 3 (to the position shown in phantom lines in FIG. 4) causes corresponding proximal movement of rod 42 and corresponding closure of jaws 46, 48. Similarly, pivotal movement of handle 18 in the proximal and upward direction as shown in solid lines in FIG. 3 causes corresponding distal movement of rod 42 with corresponding opening movement of jaws 46, 48.

At any time during such movements, the trigger 20 may be selectively actuated by the surgeon to cause the described locking mechanism to be inoperative, thereby allowing handles 18 and 16 (and therefore jaws 46 and 48) to move freely in response to the surgeon's touch. However, as mentioned above, if no pressure is applied to trigger 20, handles 18 and 16 will operate in ratcheting engagement with each other, allowing the surgeon to lock the handles (and therefore the jaws or other tool mechanism) into a given position. This position may be changed by applying pressure to trigger 20, moving handles 18 and 16 to a desired position and releasing the pressure on trigger 20. Now the handles (and jaws) have moved to a new position, into which they are locked by the ratcheting mechanism. It will be appreciated that the respective incremental selectable locking positions of the jaws can be determined by the pitch of the locking teeth, i.e. the distance between adjacent teeth. Thus, the size of the locking teeth may be varied to provide a greater or lesser number of locking positions, depending upon the nature of the surgical procedure.

In addition, there is provided slide lock 60 which, in the "off" position (FIG. 2) does not engage trigger 20. In this "off" position, the operator is free to use trigger 20 to move handles 18 and 16 toward and away from each other as described above, and as shown in FIGS. 2 and 3. When slide lock 60 engages trigger 20 (FIG. 4), lock member 32 and arcuate section 26 are prevented from engaging one another and handle portions 16 and 18 may be moved freely away from and towards each other.

Figure 4:
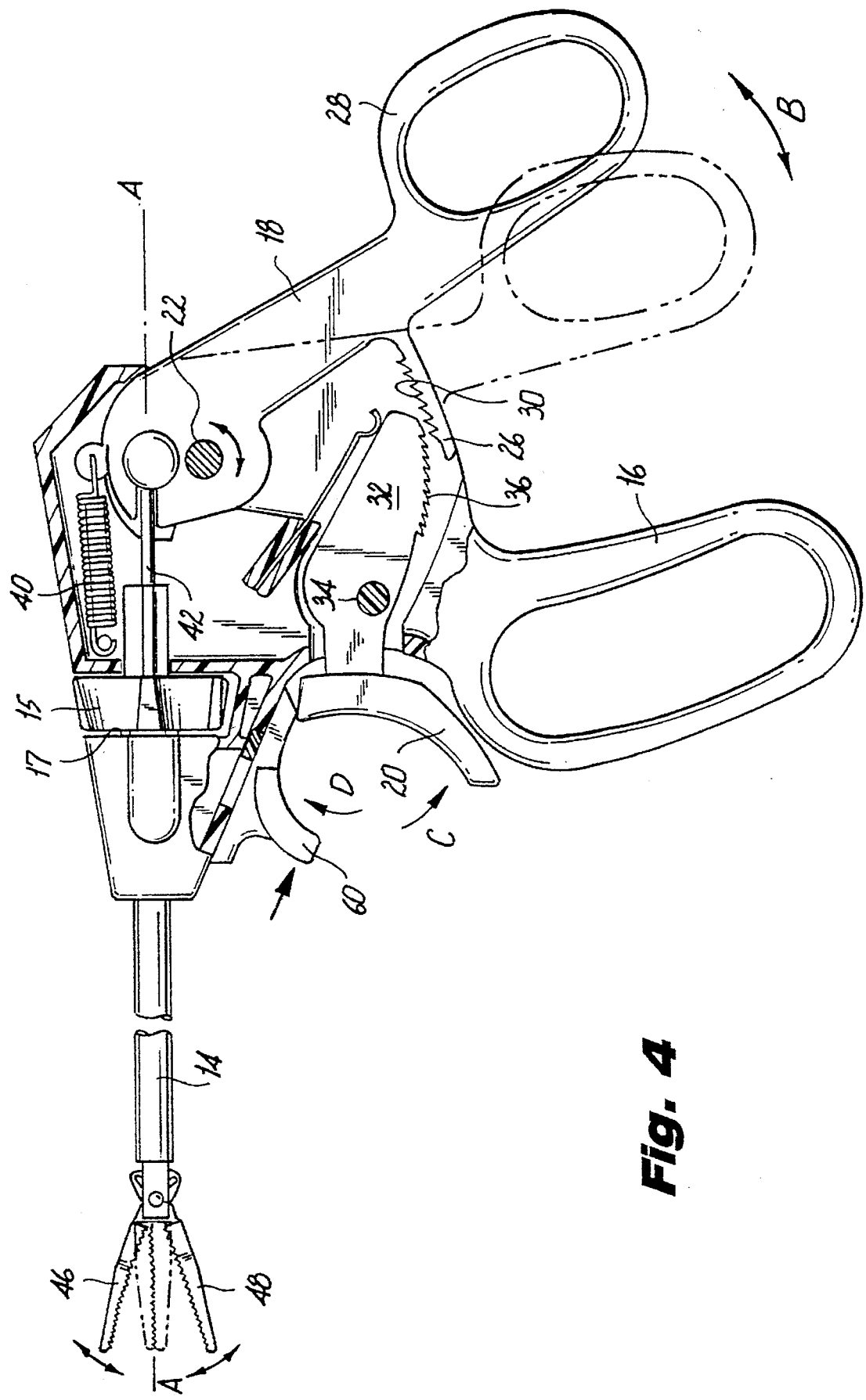
FIG. 4 is a view similar to FIG. 3 illustrating the ratchet mechanism in a released condition by the finger operable lock-out device.

Although this "non-engaged" position may be achieved through applying pressure to trigger 20, once the pressure is removed, handles 16 and 18 return to ratcheting engagement and jaws 46 and 48 are locked into position. If the surgeon wishes to move the jaws freely without applying continuous finger pressure to trigger 20, slide lock 60 may be moved proximally so that it becomes wedged under trigger 20 (as shown in FIG. 4), leaving handles 16 and 18 to move freely without applying finger pressure to trigger 20.

Referring again to FIG. 2, it will be appreciated that elongated endoscopic tubular section including rod 42 and jaws 46, 48, is rotatable about the longitudinal axis A—A by rotating finger knob 15 to which it is connected. This movement rotates the entire elongated endoscopic tubular section while rod 42 is rotatably supported about bearings 58 shown schematically in FIGS. 2–3.

It will also be appreciated that while the preferred embodiment of the surgical apparatus utilizes rod 42 to actuate, i.e. open and close a pair of jaws 46, 48 mounted at the distal end of the elongated endoscopic tubular section, such distal and proximal movement of rod 42 can be utilized to operate any surgical working member or members mounted at the distal end of the endoscopic section. Such working member or members may for example be other endoscopic surgical instruments such as scissors, arcuate graspers, single cutting blade or the like.

Although the present apparatus has been described with reference to preferred embodiments, it should be understood by those skilled in the art that various modifications in form and detail may be made without departing from the scope and spirit of the development. Accordingly, modifications such as those suggested above, but not limited thereto, should be considered to be within the scope of the disclosure and the appended claims.

What is claimed is:

1. An endoscopic or laparoscopic surgical instrument which comprises:
   a) a handle assembly including a barrel portion, a stationary handle and a pivoting handle extending from the barrel portion, the barrel portion having an interior cavity accommodating at least a portion of the pivoting handle, the stationary handle having an interior cavity, the pivoting handle having a lower portion forming ratchet teeth;
   b) a body assembly comprising a pair of coaxial members attached at one end to the barrel portion, and including an inner rod member slidable within an outer tube member in response to movement of the pivoting handle, the body assembly terminating at one end remote from the handle assembly in a reciprocatingly movable tool mechanism; and
   c) a ratchet assembly operatively associated with the body assembly to provide incremental movement of the tool mechanism, the ratchet assembly including a trigger attached to the stationary handle and having trigger ratchet teeth for engagement with the ratchet teeth of the pivoting handle; and
   d) an override member that prevents engagement of said ratchet teeth when said override member engages said trigger.

2. The surgical instrument according to claim 1, wherein said override member is slidably disposed on said body member.

3. The surgical instrument according to claim 1 wherein the pivotable handle activates the rod member such that movement of the pivotable handle slidingly reciprocates the rod member within the tube member.

4. The surgical instrument according to claim 1, wherein the ratchet assembly is spring biased to a disengaged position.

5. The surgical instrument according to claim 1, wherein the ratchet assembly is spring biased to an engaged position.

6. The surgical instrument of claim 1 further comprising spring means disposed within the interior cavity of the barrel portion operatively associated with the pivoting handle for biasing the ratchet teeth of the pivoting handle into engagement with the trigger ratchet teeth.

7. The surgical instrument according to claim 1, further comprising a circumferentially disposed knob member positioned on the body assembly and extending outwardly through a slot on the barrel portion of the handle assembly, the knob member providing for rotational movement of the body assembly.

8. The surgical instrument according to claim 1, wherein said tool assembly further comprises a pair of jaws.

9. A handle assembly for endoscopic and laparoscopic surgical instruments, the instrument including a body assembly secured to the handle assembly and having an inner rod member coaxially slidable within an outer tube member, the instrument further including a tool mechanism secured at an end of the body assembly distal from the handle; the handle assembly comprising:
   a) a pivoting handle operatively associated with the body assembly for moving the tool mechanism between an open and closed position;
   b) a stationary handle having an interior cavity;
   c) a disengagable ratchet assembly operatively associated with the pivotable handle to provide incremental movement of the tool mechanism when the ratchet assembly is in an engaged position, and free movement of the pivoting handle when the ratchet assembly is in a disengaged position; and
   d) a slide lock operatively associated with the ratchet assembly for maintaining the ratchet assembly in disengaged position.

10. The handle assembly of claim 9 wherein the ratchet assembly includes a plurality of ratchet teeth formed by a lower portion of the pivoting handle.

11. The handle assembly of claim 10 further comprising a trigger pivotably secured to the stationary handle, the trigger having a plurality of trigger ratchet teeth, the trigger being spring biased to engage the trigger ratchet teeth with the ratchet teeth of the pivoting handle, the trigger configured to pivotably disengage the trigger ratchet teeth from the ratchet teeth.

12. The surgical instrument according to claim 9, further comprising a circumferentially disposed knob member positioned on the body assembly and extending outwardly through a slot on the barrel portion of the handle assembly, the knob member providing for rotational movement of the body assembly.

13. An endoscopic or laparoscopic surgical instrument comprising:
   a) a handle assembly including a barrel portion, stationary handle and a pivoting handle;
   b) a body assembly comprising a pair of coaxial members attached at one end to the handle assembly, including an inner rod member slidable within an outer tube member in response to movement of the pivoting handle of the handle assembly, the body assembly terminating at an end remote from the handle assembly in a reciprocatingly movable tool mechanism; and
   c) a first toothed ratchet mechanism associated with the pivoting handle;
   d) a second toothed mating ratchet mechanism operatively associated with the first toothed ratchet mechanism for selectively locking the first toothed ratchet mechanism and the pivoting handle in one of a plurality of selectable positions to thereby position the inner rod member and the movable tool mechanism in predetermined selectable positions; and
   e) a trigger operatively associated with the second toothed ratchet mechanism for selectively engaging and disengaging the first and second ratchet mechanisms to thereby selectively lock and unlock the movable tool mechanism.

14. The surgical instrument according to claim 13, wherein said tool mechanism further comprises a pair of jaws.

* * * * *